United States Patent [19]
Li et al.

[11] Patent Number: 5,778,681
[45] Date of Patent: Jul. 14, 1998

[54] COOLING DEVICE FOR COOLING HEATABLE GAS CHROMATOGRAPHY ANALYTE SAMPLE INJECTOR

[75] Inventors: Kenneth Li, Piedmont; John Robinson, Concord, both of Calif.

[73] Assignee: Varian Associates, Inc., Palo Alto, Calif.

[21] Appl. No.: 838,148

[22] Filed: Apr. 15, 1997

[51] Int. Cl.$^6$ .................................................. F17C 9/02
[52] U.S. Cl. ...................................... 62/50.2; 62/51.1
[58] Field of Search .............................. 62/50.2, 51.1

[56] References Cited

U.S. PATENT DOCUMENTS

| | | | |
|---|---|---|---|
| 2,945,354 | 7/1960 | Moskowitz | 62/50.2 |
| 3,077,745 | 2/1963 | Grantham et al. | 62/50.2 |
| 4,054,056 | 10/1977 | Wegstedt et al. | 73/190 R |
| 4,091,672 | 5/1978 | Amrine et al. | 73/343 |
| 4,174,619 | 11/1979 | Tocha | 62/50.2 |
| 4,269,608 | 5/1981 | Sisti et al. | 55/67 |
| 4,474,588 | 10/1984 | Hinshaw, Jr. | 55/197 |
| 4,477,266 | 10/1984 | Yang et al. | 55/67 |
| 4,847,469 | 7/1989 | Hofmann et al. | 219/273 |
| 4,861,989 | 8/1989 | Vestal et al. | 250/288 |
| 4,888,199 | 12/1989 | Felts et al. | 427/10 |
| 4,948,389 | 8/1990 | Klein et al. | 55/20 |

OTHER PUBLICATIONS

Varian Associates, Inc., "*1078 Universal Capillary Injector Brochure*", Jun. 1995.
Woolfenden et al., "The impact of innovative technology on GC cost of ownership", *American Library*, pp. 18I–18M; 18J; Jul. 1996.
Jessie Crockett Butler, "*TR 9122 Product Analysis—Simplified Design of a Temperature Programmable Multi–mode Injection GC Inlet System Brochure*", 1996.
Varian Associates, Inc., "*Septum–Equipped Programmable Injector (SPI)*", 1996.
Varian Associates, Inc., "*1078 Universal Capillary Injector Operator's Manual*", 1997.

*Primary Examiner*—Ronald C. Capossela

[57] ABSTRACT

The present invention is an improved modular cooling device for cooling gas chromatography analyte sample injectors. The invention is embodied in a series of tubes connected in fluid communication from a coolant supply valve to the injector heating block. A flexible supply tube capable of carrying coolant while maintaining structural integrity at temperatures up to about 150° C., and having a low thermal conductivity is connected in fluid connection with a coolant supply at one end, and a transition tube at the other. A transition tube, in fluid communication with the supply tube at one end and with the cooling tube at the other, is selected to maintain structural integrity at temperatures up to 450° C. and to have a low thermal conductivity. The cooling tube is in fluid communication with the transition tube at a receiving end and with an exhaust at an exhaust end, and has an outer surface that is physically engageable with a surface of the heating block. The cooling tube is capable of maintaining structural integrity at temperatures up to 450° and has a high thermal conductivity (at least about 200 watts/meter ° C.) to facilitate heat transfer. The cooling tube further has a flattened surface for creating a greater surface area for physical engagement with the heating block to provide greater cooling effect.

26 Claims, 8 Drawing Sheets

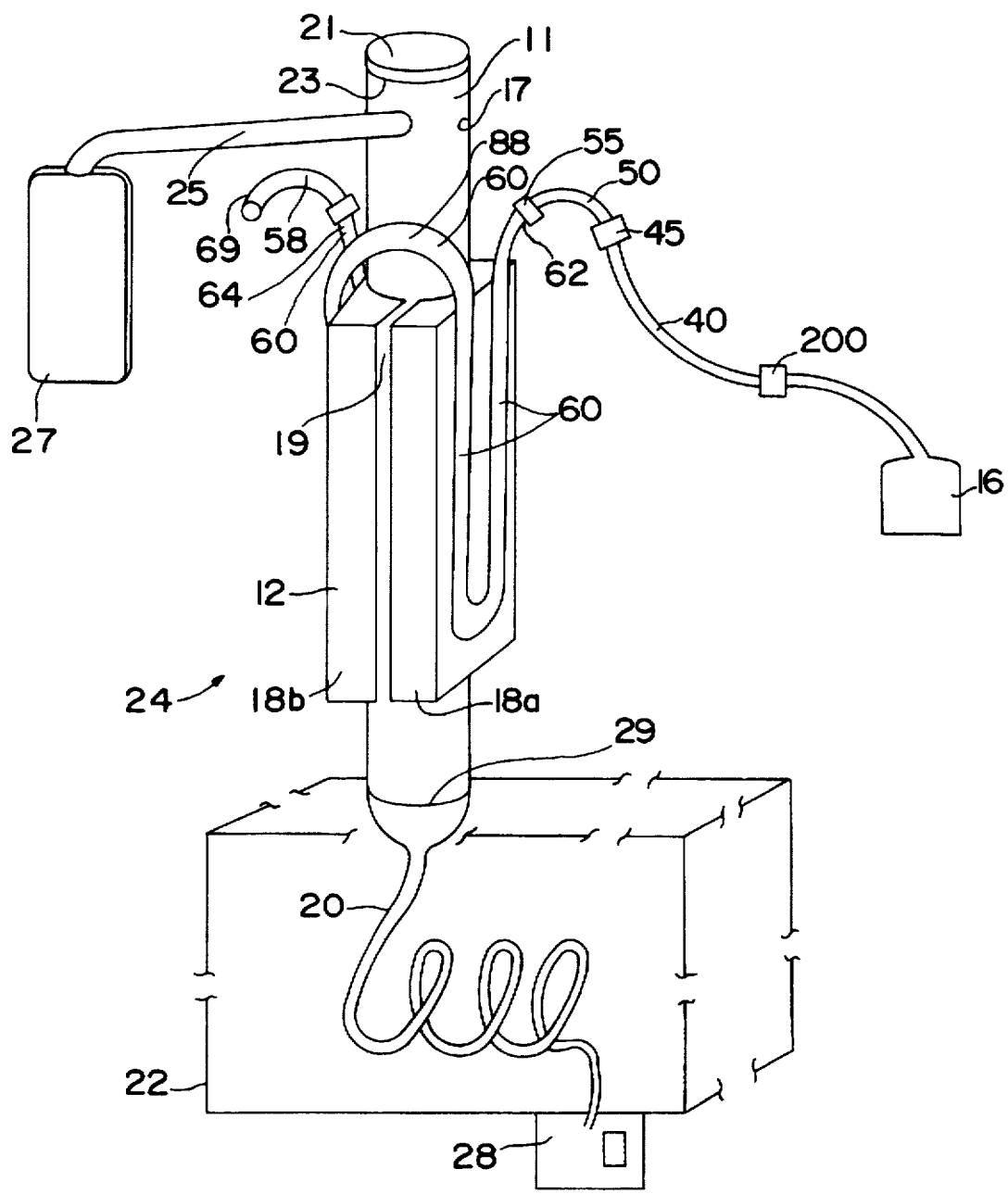
FIG. IA

5,778,681

COOLING DEVICE FOR COOLING HEATABLE GAS CHROMATOGRAPHY ANALYTE SAMPLE INJECTOR

FIELD OF THE INVENTION

The present invention relates to an improved cooling device for cooling gas chromatography analyte sample injectors and more specifically to an improved cooling device for cooling gas chromatography analyte sample injector heating blocks.

BACKGROUND OF THE INVENTION

Gas chromatography is used for a wide variety of qualitative and quantitative analytical applications to determine the nature and relative concentrations of substances that are present within a sample. For example, environmental analysis may make use of gas chromatography to determine what pollutants might be present, and their relative concentrations, in a sample of soil or water. Another application of gas chromatography is in the area of blood testing. In particular, testing of fluid from blood samples through gas chromatography can be used to test for the presence of drugs.

In gas chromatography, the sample undergoing analysis is volatilized and passed through a column by a carrier gas. The sample is injected into one end of the column and separated into its constituent components, referred to as analytes, as it is carried to a detector at the other end. Typically, a coating on the inside of the column provides an affinity gradient with respect to substances present in the analyzed sample. Thus, as the analyte is moved through the column, substances within the sample will separate, as those with higher affinity with respect to the column coating linger against the column wall, while those with lower affinity move through the column with less interaction with the column wall coating. A variety of detectors are available to detect substances as they are emitted from the detector end of the column. Such detector devices are known to those skilled in the art and are not discussed in detail herein. Upon detection, a signal is generated to plot a graph showing a peak for a particular substance.

Gas chromatography is typically performed in an environment in which the temperature is controlled, typically within the range of 50° to 450° C., so that the tested material is maintained in a gaseous state. Accordingly, the column through which the analyzed sample is carried is situated in a gas chromatography oven so that the column may be maintained at a desired temperature. In some applications, it is desirable to vary the temperature of the column while the sample moves through the column. Varying the temperature can be a means to speed the analysis time for a given sample. Varying the temperature can also serve as a means to provide more efficient gas chromatographic analysis, for example, by providing greater resolution of analyte presence and concentration representations in the gas chromatogram produced by the detector. Typically such temperature variation or programming is effected by computerized control of the oven temperature. Computerized control to the temperature programming during the course of a single analysis or over the course of multiple analyses has been found to provide reduced analysis time, increased efficiency of the analysis procedures, and cost reduction in carrying out such processes. Other factors can also be varied, such as the coating on the column, the flow rate of the carrier gas, and the detector, in order to obtain greater differentiation in peak formation and resolution to allow more accurate determination of the materials and concentrations of detected substances. Moreover, computerized programming has been used to perform reproducible programs of heating to carry out multiple standardized analyses.

As many analyzed materials are not in a gas phase prior to undergoing gas chromatographic analysis, it is necessary to include means for volatilizing the sample, which is typically a liquid solution. This is done through an injector assembly which includes an injector flow passage, a heatable zone along the passage, and a heating means to heat the heatable zone. The injector assembly has an inlet at one end through which a flow stream of carrier gas is received, and an outlet which is in fluid communication with the column, through which the flow steam is released for carrying an analyte sample through the column. The injector further has a means for the controlled introduction of analyte sample near the carrier gas inlet. Typically, the injector has a septum which is penetrable by a hollow needle, and analyte sample is introduced into the injector by introduction of the needle through the septum and discharging analyte sample into the heatable zone of the injector pathway. Alternatively, the analyte sample can be introduced in to the heatable zone of the injector flow passage through a valve.

Typically, the heatable zone of the injector passage is heated by a heating means, often in form of an injector heating block suitably shaped and of suitable material to develop a desired thermal profile within the heatable zone of the injector flow passage. The heating block of the injector can be a unitary, or monolithic block, or, alternatively, maybe a split block, with block components sandwiched together around injector flow passage within the injector. The injector assembly and the heatable zone of the injector flow passage, and the heating block are typically situated outside of the oven, but in close proximity, such as the outside wall of the oven, to permit fluid connection of the injector flow passage to the column, the latter of which is situated within the oven.

The temperature of the heating block must be sufficiently high, to vaporize the solvent and analyte, which are then drawn, by the flow of the carrier gas, into the gas chromatography column. Most gas chromatography injection can be done using an injector at constant and sufficiently high temperature. Yet, in many practical applications, it is desired to have the injector initialized at a first temperature, or initialization temperature, then heated to a final higher temperature at a programmed rate following complete injection of the analyte sample. Further, it is desired to raise the temperature of the heatable zone of the injector flow passage at a reproducible program, to carry out gas chromatography analysis where the program of heat ramping of the injector is identical to a predetermined or previously utilized program. Injection methods utilizing programmed temperature ramps are preferable for samples containing, for example, thermally labile analytes or a mixture of analytes with widely ranging boiling temperatures. The cooling device of the present invention is of particular importance to these applications which utilize temperature ramping from an initial temperature to a final temperature and in which repeated temperature ramping and computer controlled temperature ramping in the carrying out of multiple gas chromatographic sample analyses is desired.

Typically, the block is heated from the initialization temperature over a temperature "ramp" during a predetermined period of time to a higher temperature plateau. The block may be again heated over multiple ramps, to multiple temperature plateaus. Ultimately, the block is heated to a predetermined final temperature, which may be the first plateau temperature, where the temperature of the block is maintained until the analyte is vaporized and carried, by the flow stream of the carrier gas, into the column. In common practice, the setting of the initialization temperature of the block, the ramping of the temperature of the block, and the holding of the block at a final higher temperature are all carried out by computerized control in a reproducible manner. The block itself is heated by a heating element which is in turn controlled by computer output. The block temperature is monitored with a temperature sensor, which has a feedback input to the computer control, so that the heat provided by the heating element is regulated by the computer to achieve the desired temperature ramping of the block.

The pattern of heating of the block and the oven are factors which are chosen, along with other factors, such as the type of detector, the rate of flow of the carrier gas, and the column coating, according to a regimen or "method" designed by the analyst utilizing the gas chromatography procedure with the goal of yielding a particular type of analysis.

In practical applications, gas chromatography analysis often requires multiple chromatography procedures on multiple samples to yield a meaningful evaluation of a particular series of samples. One such example is in environmental testing, where a large number of samples are taken over a period of time or over a geographical region. Multiple successive operations of the gas chromatography apparatus are also required in other applications where a large number of unrelated samples must be tested, such as a blood analysis and drug screening operations.

To carry out such multiple chromatography procedures, repeated cycling of the gas chromatograph and the injector from initial state, through an analysis during which high temperatures are attained, and then back to an initialization state, which may call for the injector flow passage being at or even below room temperature. Thus, the need for efficiently cooling the heatable zone of the injector flow passage has become important in particular gas chromatography applications. To cool the heatable zone of the injector flow passage, it is necessary to cool the heating block adjacent to it, as the high temperature of the block imparts heat to the heatable zone of the injector flow passage. Certain applications of gas chromatography analysis require accurate and swift initialization of the temperature of the block. With the process over for a particular analyte sample, the gas chromatograph apparatus must be readied to begin analysis of a new sample. Once the injection is completed and the chromatography procedure is done, the injector must be cooled from the high injection temperature back to the initialization temperature. Because of the high temperatures which the block of the injector and the heatable zone of the injector flow passage may be heated to, for example, 450° C., a significant application of cooling can be required to bring the block and thus the injector back to an initialization temperature. Significant application of cooling takes time and thus puts constraints on the overall efficiency of operation of a particular gas chromatography apparatus or application process. Moreover, significant application of cooling takes significant application of coolant, which adds to the cost of such gas chromatography procedures. Therefore, there is need for rapid and efficient cooling of the heatable zone of the injector flow passage and of the heating block.

Cooling devices for heating block injectors are known. In such devices, a coolant is delivered to the heating block. Typical coolants are coolant fluids, such as liquid carbon dioxide ($LCO_2$) or compressed air, or a cryogen, such as liquid nitrogen ($LN_2$). A known device for delivering coolant to the heating block is through an internal cooling fluid channel within the block itself, such as in the cooling device used in conjunction with the 1093 SPI injector assembly manufactured by Varian Associates, Inc., assignee of the present invention. While this method has certain advantages, there are engineering constraints in putting a channel within the block itself, which has other structures which also must be incorporated within it, such as a pathway for the analyte sample to flow through and be heated, and a receptacle for a heating element so that the block may be heated to the required temperature. These engineering constraints add time and cost to manufacture, neither of which are required or are desired in applications where cooling is not required. Yet, standardization of the injector assembly and heating blocks in a modular fashion is desired to provide flexibility to the end user and lower engineering and manufacturing costs. Therefore, a continuing need exists for a modular cooling device which may be installed to work in conjunction with a preexisting non-cooled injector heating block, or which may be utilized as an optional feature to an otherwise non-cooled injector heating block.

Modular cooling devices for cooling the heating block are known, for example the 1078 injector, manufactured by Varian Associates, Inc., which is available with an exterior cryogen tube, Cryogenic Inlet Tube Varian #03-918673-00, which is essentially a continuous stainless steel tube, of circular cross-section, connected at one end to a coolant source and mounted so that the outside surface of the cryogen tube contacts one heating block component. This device has the major advantage of allowing operation without the cooling apparatus, while permitting the same equipment to be fitted with a cooling device for applications where cooling is required.

Nonetheless, this type of cooling device is also subject to design limitations. Physical contact between the essentially round outside wall of the coolant tube and the essentially flat surface of the block causes heat exchange to take place along a very small portion of the exterior wall of the coolant tube, rendering such a system inherently inefficient. Moreover, even along the area of contact between the outside wall of the coolant tube and the surface of the block, imperfections in contact between the outside of the cooling tube and the heating block limit the heat exchange between the heating block and the coolant within the cooling tube. At these areas of imperfect contact, the local heat transfer mode degenerates from a relatively effective solid-to-solid thermal conduction, to poor heat transfer through the resulting air gap.

Another limitation of the prior art cooling device is that heat exchange between the block and the coolant must overcome the thermal conductivity limitations, or insulating effect, of the cooling tube in which the coolant is carried. Due to the harsh environment of the region of the heating block, the cooling tube must also remain operable, that is, maintain its structural integrity, withstand the potential for structurally degrading oxidation, and otherwise perform at high temperatures, for example, up to 450° C., and at low temperatures, for example while carrying a coolant, which may be at a temperature below minus 100° C. These factors have led to the use of a coolant delivery pathway of essentially a single tube, or a single component of tubing, to supply and cool the block, configured to accommodate both the low temperature of coolant, the high temperature of the heating block, durability to withstand repeated temperature cycling, minimizing cost of manufacture, ease of procurement, ease of installation, and other factors. In such known systems, a delivery tube favoring structural integrity at the expense of thermal conductivity, has been constructed from stainless steel having a thermal conductivity in the range of 15 watts/meter ° C. over the entire length of this delivery pathway, from the coolant source to the injector heating block. When compared to known cooling devices in which the block has an internal cryogen cooling channel, the known exterior coolant delivery systems have had significantly less cooling capability, requiring two to five times the cooling time and up to over six times the amount of coolant. Thus, a continuing need exists for an improved cooling device with a coolant delivery pathway that can carry coolant adjacent to the heating block to cool the heating block, that can quickly and efficiently cool the heating block of a gas chromatography heating injector to permit maximum applicability of a single block design, and which permits a user to have a lower cost non-cooled block adapted for cooling.

SUMMARY OF THE INVENTION

The present invention encompasses an improved modular cooling device which can rapidly cool the gas chromatography analyte sample injector in applications where the injector is heated to volatilize an analyte sample. Broadly stated, the device of the present invention presents a significant improvement to the cooling efficiency that has heretofore been attainable in modular devices for gas chromatography systems.

The improved cooling device of the present invention is embodied in a tube arrangement through which coolant is delivered to the injector, and in particularly the injector heating block. The tube arrangement satisfies the requisite functions of carrying coolant from a coolant source, which may be kept remote from the gas chromatagraph device and the region of the heating block, which heats the heatable zone of the injector flow passage, at which temperatures as high as 450° C. may be attained. The tube arrangement of the present invention further has the advantages of minimizing the barriers to efficient cooling which arise from the heat transfer inhibition due to the insulating effects of a coolant tube wall and the intervening space between the outside of the coolant tube wall and the heating block surface.

The cooling device of the present invention is embodied in a tube arrangement including supply tube, to carry coolant to the region of the heatable zone of the injector flow passage, and a cooling tube, in fluid communication with the supply tube and engageable in at least partial physical contact with a heated portion of the injector, such as the injector heating block, to carry coolant from the supply tube to the injector. In operation, the supply tube is connected in fluid communication with a source valve, the valve supplying coolant fluid to the supply tube from a remote coolant fluid tank. The supply tube has a generally high degree of flexibility, to reduce space limitations in the area of the gas chromatography device and permit remote location of the valve, through which coolant is introduced into the supply tube, and a relatively low heat conductivity, to minimize warming of the coolant, and thus maintain the coolant as cold as possible before it reaches the area of the heating block. The cooling tube may have a lower flexibility than the supply tube, so that it can retain a particular contour imparted to it, thus permit a predetermined configuration of contact between the outside wall of the cooling tube and the heating block when the cooling tube is engaged with the block. The cooling tube further has a higher level of heat conductivity than the supply tube, thus reducing the insulating effect of the tube wall itself in the region of the heating block. Ideally, the cooling tube is designed to have a composition in the range of 99.90–99.99% by weight of silver (Ag) to further minimize the insulating effect of the cooling tube wall itself, while maintaining structural integrity within the temperature ranges of the heating block at its extremes.

In another embodiment, the cooling device of the present invention comprises an arrangement of three tubes, a supply tube, a transition tube in fluid communication with the supply tube, and a cooling tube in fluid communication with the transition tube and engageable in at least partial physical contact with a gas chromatography analyte injector heating block. In this embodiment, the supply tube has a high degree of flexibility to provide greater adaptability within the often cramped environment of the gas chromatography device and allow for various physical orientations between a coolant fluid source valve and the injector. The supply tube further has a low heat conductivity and acts as an insulator to keep the cooling fluid as cold as possible before it reaches the area of the heating block. The transition tube carries the cooling fluid to a region adjacent to the heating block. The transition tube may be less flexible than the supply tube, so that it can retain a particular configuration imparted to it, and is constructed to withstand the temperature ranges of the heating block to allow it to come close to the heating block for connection with the cooling tube. The transition tube further has a low thermal conductivity to insulate the coolant fluid from the thermal energy of the heating block as well as insulate the supply tube from the thermal energy of the heating block. Use of such a transition tube allows greater latitude in selecting materials for the supply tube to minimize thermal conductivity of the supply tube. The cooling tube has a higher level of heat conductivity than the transition tube and supply tube, to maximize heat transfer between the heating block and the coolant fluid as the coolant fluid is carried, within the cooling tube, adjacent to the heating block, for cooling the block, while heat transfer to the coolant fluid is minimized as it is carried through the supply tube and the transition tube to the cooling tube.

In a further aspect of the invention, the cooling tube is modified to an out of round configuration, to create flattened areas of the outer wall of the cooling tube. The flattened areas increase the surface area contact between the outer wall of the cooling tube and the surface of the heating block. The flattened areas of the outer wall further bring a greater proportion of the cooling fluid, flowing through the cooling tube, physically closer to the block itself than a substantially fully round conventional tube. The flattened areas of the outer wall further allow a firmer physical contact to be achieved between the outer wall of the cooling tube and the heating block, reducing the intervening space between the outer wall of the cooling tube and the heating block, thus reducing the amount of insulating air between the two. The flattening of the cooling tube has the added advantage, in the case of pressurized coolants, such as $LCO_2$ of restricting expansion of the cooling fluid, thus reducing the instance of "snow" which can occur when pressurized coolant, such as $LCO_2$, expands at an excessive rate to vaporization with a cooling effect that actually freezes a portion of the coolant. Reduction of cryogen "snow" increases the efficiency of the cooling apparatus.

In a further aspect of the invention, the cooling tube is received in a channel defined by the heating block to further increase heat exchange between coolant within the cooling tube and the heating block.

Accordingly, it is an object of the present invention to provide a modular cooling device for cooling a gas chromatography analyte injector that can cool with greater efficiency, that can cool faster and with a lower usage of cooling energy.

It is another object of the present invention to provide a cooling device for cooling a gas chromatography analyte sample injector heating block, that is external to the heating block so that it can be added as an optional feature to an injector that has no cooling apparatus, and that can cool with greater efficiency.

It is another object of the present invention to provide a cooling device for cooling a gas chromatography analyte sample injector heating block, that utilizes a multi-component cooling fluid delivery pathway, comprising a supply tube and a cooling tube in fluid communication with the supply tube and in at least partial physical contact with the surface of the heating block, in which the supply tube is configured to maximize structural integrity, insulation and flexibility at temperatures up to about 150° C. and the cooling tube is configured to maximize heat exchange in the area of the heating block which is to be cooled.

It is another object of the present invention to provide a cooling device for cooling the heating block of a gas chromatography analyte sample injector, that utilizes a multi-component cooling fluid delivery pathway, comprising of a supply tube, a transition tube in fluid communication with the supply tube, and a cooling tube in fluid communication with the transition tube and in at least partial physical contact with the surface of the heating block, in which the supply tube is configured to maximize insulation and flexibility at temperatures up to about 150° C., the transition tube is able to withstand temperatures of up to 450° C. while also minimizing heat transfer to prevent heating of the cooling fluid, or adversely compromise the structural integrity of the supply tube, and the cooling tube is configured to maximize heat exchange in area of the heating block which is to be cooled.

These and other objects of the present invention will become apparent to those skilled in the art from the following detailed description of the invention, the accompanying drawings, and the appended claims.

BRIEF DESCRIPTION OF THE DRAWINGS

FIG. 1a is a partial perspective—partial schematic drawing of the cooling device according to the present invention.

FIG. 5a is a schematic of heat transfer in a known cooling device; FIGS. 5b–5c are schematic representations of heat transfer in various embodiments of the cooling device according to the present invention.

DETAILED DESCRIPTION OF THE INVENTION

Figure 1:
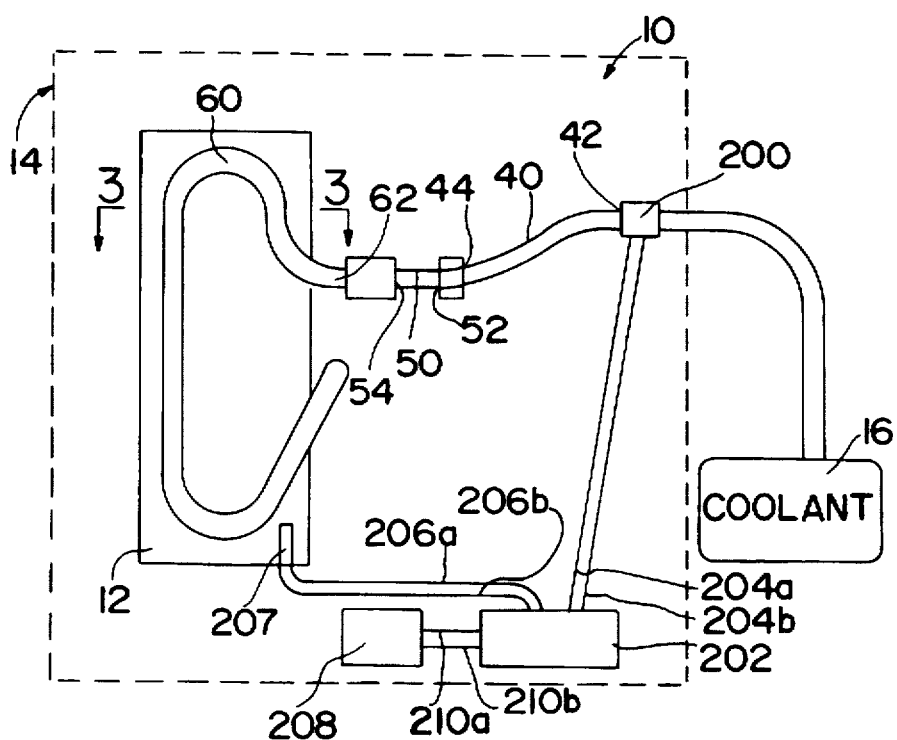
FIG. 1 is a schematic drawing of a cooling device according to the present invention.

Referring to FIG. 1, the present invention is directed to a cooling device 10 for cooling a heating block 12 of a gas chromatography apparatus 14 by delivering a cooling fluid from a cooling fluid source 16 in order to cool the block 12. The block 12 is a split block sandwich consisting of block sections 18a and 18b. The gas chromatography apparatus 14 includes a column 20, housed within an oven 22. An injector assembly 24 is situated on the exterior of the oven 22 and is in fluid communication with the column 20 at the inlet end 26 of the column 20. A detector device 28 is located at the outlet end 30 of the column 20 to detect analyte (not shown) which has traveled through the column. Many types of detectors, well known to those skilled in the art, may be used, and the specific detector is not important to the present invention.

With specific reference now to FIG. 1a, the injector assembly 24 includes a wall 11 defining an injector flow passage 17. The injector assembly further includes the heating block 12, and in use, the heating block 12, which may be a block sandwich of block sections 18a and 18b, is engaged with, or sandwiched in physical engagement upon, the injector wall 11. The injector further has a heatable zone 19 defined by the injector wall in the region of engagement with the heating block. A septum 21 is fitted within an injection opening 23 defined by the injector wall 11. A carrier gas inlet 25 permits a carrier gas to flow from a carrier gas source 27 into, and through, the injector flow passage 17. An outlet end 29 of the injector flow passage 17 is connected to the column 20, and the carrier gas is permitted to flow through the injector flow passage 17 into the column 20.

In one embodiment of the present invention, a supply tube 40, having a first end 42 and a second end 44, is connectable, in fluid communication, at its first end to the cooling fluid source 16 through source valve 200. The second end 44 of the supply tube 40 is connected, in fluid communication to a transition tube 50, the transition tube having a supply end 52 and a transmission end 54, the supply tube 40 connected to the supply end 52 of the transition tube 50. A cooling tube 60, having a receiving end 62 and an exhaust end 64, is connected, at its receiving end, in fluid communication with the transition tube 50. An exhaust 69 is connected, in fluid communication, with the cooling tube 60 at the exhaust end 64 of the cooling tube 60.

The coolant supply may be a tank of coolant, for example liquid carbon dioxide ($LCO_2$) or liquid nitrogen ($LN_2$). Alternatively, the supply may be a valve 200 to which coolant is delivered from a remote tank or source. Preferably, the valve is located in a proximity to the gas chromatography injector so that the supply tube and transition tube do not need to be overly long.

Referring now again to FIG. 1, a computer 202 is connected by input and output lines 204a and 204b with the valve 200 to provide for computer operation of the valve 200. Input and output lines 206a and 206b connect the computer 202 with a heat sensor 207 which is mounted in engagement with the heating block 12, to enable the computer to carry out control of the valve 200 based upon a monitored temperature of the heating block. A user interface 208 is provided in the gas chromatograph which is connected by input and output lines 210a and 210b to permit a user to program the computer to carry out a particular program of temperature control of the cooling device, which may be a reproducible program.

The valve 200 may be a binary, either being open or closed, pulsed valve, so that the rate of cooling fluid flow introduced through the valve into the supply tube is regulated by the percentage of time the valve is held open by the computer 202 which carries out preprogrammed cooling. In $LCO_2$ applications, the volumetric capacitance downstream of the valve shut-off point must be small in order for the response of coolant delivery with respect to valve open time to be linear. Linear relation between the amount of coolant delivered and the time duration during which the valve is open permits predictable cooling fluid flow through the cooling device and thus predictable cooling control of the heatable zone of the injector flow passage by computer control. Minimizing the excess volume imparted by the valve is desired in $LCO_2$ applications to prevent expansion within the supply tube.

To maximize flexibility and the adaptability of the supply tube to a cramped environment, it is preferably configured of a plastic or polymer. A flexible tube permits simple, in-the-field installation of the cooling device of the present invention to a gas chromatography injector that has not previously been equipped with a cooling device. Use of a plastic or polymer supply tube allows the installer to customize the supply tube to a particular predetermined length by use of a simple cutting device, such as a scissors or a razor blade.

It is preferable that the supply tube have a low thermal conductivity, to reduce heat exchange between the cooling fluid and the supply tube itself as well as between the coolant and the environment through which the supply tube must pass in supplying coolant to the cooling tube. Use of a plastic or polymer construction of the supply tube aids keeping the thermal conductivity of the supply tube low, thus insulating the coolant as it is supplied. Where the coolant that is used is $LCO_2$, it is further desired to configure the supply tube to have a high tensile strength and a high level of resiliency. This is because the $LCO_2$ cooling fluid must be kept under pressure to maintain its liquid state, and thus its potential to cool when pressure is reduced. In $LCO_2$ applications, the supply tube is preferably configured of PEEK (polyetheretherketone) tubing, which has excellent tensile strength over wide temperature ranges and is also highly resilient. In one embodiment of the present invention, the supply tube has been configured of PEEK with an inside diameter (I.D.) of 0.015 inches and an outside diameter (O.D.) of 0.063 inches (1/16 inches). The length of the supply tube is adapted to allow the pressure drop, which allows the $LCO_2$ to expand and cool, in the cooling tube substantially in the region adjacent to the injector heating block.

In cases where $LN_2$ is used, pressure restriction is not necessary, and the supply tube may be configured of a high performance plastic, such as polytetrafluoroethylene (e.g., Teflon® or variations thereof, such as TFE). With the lower pressure involved in supplying $LN_2$, an embodiment in which the dimensions of the supply tube are 0.125 inches I.D. and 0.185 inches O.D. has been used.

The supply tube 40 is connected at its second end 44 to the supply end 52 of the transition tube 50. For $LCO_2$ applications, a connector 45 with a low internal volume is preferable, to minimize the potential for creation of a pressure drop. Because of the high pressure desired to be maintained to prevent expansion of the coolant, a commercial union designed for 1/16 inch O.D. has been used. With a supply tube and a transition tube both having 1/16 inch O.D. and 0.015 inch I.D., a connector connecting tubes of same O.D. and I.D. can be used, in which the I.D. is kept substantially constant through the connection, and in the case of $LCO_2$, the connector thus contributes partially to flow restriction. One connector that has been used is a ZU1 union manufactured by VALCO Instruments, which has the preferable low internal volume and an internal diameter substantially similar to that of the supply and transition tubes. For $LN_2$ applications, a connector with a low heat capacity is preferable, although no particular configuration is required. A simple hose clamp has been used.

The transition tube 50 carries coolant from the supply tube to the region of the heating block 12. Because temperatures in the region of the block 12 can be as high as 450° C., it is desirable to configure the transition tube to withstand such temperatures. The transition tube 50 extends between the supply tube 40 and the cooling tube 60. It is preferably somewhat rigid, so it can hold a particular physical orientation. The transition tube is designed to maintain pressure as well as maintain flow restriction to the cooling tube in $LCO_2$ coolant applications, and to minimize heat exchange transfer to the coolant, whether $LCO_2$ or $LN_2$. Preferably, the transition tube is configured of stainless steel.

In applications where $LCO_2$ is the cooling fluid, the transition tube preferably has the same I.D. as the supply tube. In an embodiment that has been used, the transition tube I.D. is 0.015 inches, with an O.D. of 0.063 inches. Further, in $LCO_2$ coolant applications, it is preferable that the ratio of the length of the supply tube to the length of the transition tube be large, for example 9:1. In one embodiment, supply tube length has been about 18 inches, with a transition tube length of 2 inches. The transition tube is preferably of a length no longer than needed to thermally isolate the supply tube from the extreme temperature of the block. Because $LCO_2$ provides cooling effect by its latent heat of expansion (from a supply at approximately 900 psi), it is preferable to have the expansion point positioned inside the cooling tube 60 near the heating block 12 to maximize the cooling effect of the $LCO_2$ coolant on the block.

In $LN_2$ coolant applications, a transition tube having an I.D. of 0.094 inches and an O.D. of 0.126 inches has been used. The transition tube in $LN_2$ applications may be oriented into an elbow 58.

The cooling tube has an inside surface 66 and an outside surface 68. In one embodiment, the diameter of the inside surface 66 of the cooling tube, that is the I.D. of the cooling tube, is 0.066 inches. In this embodiment, the diameter of the outside surface 68 of the cooling tube, that is the O.D. of the cooling tube, has been 0.109 inches. An object of the present invention is more efficient heat transfer between the coolant and the heating block which is to be cooled. To achieve this object, the cooling tube is configured to maximize both thermal conductivity and heat conduction effect between the coolant within it and the heating block. Preferable thermal conductivity is at least 200 watts/meter ° C., calculated at approximately room temperature, and believed to be substantially maintained at temperatures up to and including temperatures about 450° C. This includes metals such as aluminum, copper, silver and gold, but does not include stainless steel, which has a thermal conductivity of approximately 15 watts/meter ° C.

The cooling tube is connected, at its receiving end 62, to the transmission end 54 of the transition tube by connection 55. The connection between the transition tube 50 and the cooling tube 60 can be made in any number of known connections, although brazing is preferable. In the case of the preferred $LCO_2$ transition tube, the outside diameter of the transition tube 50 is smaller than the inside diameter of the cooling tube 60. This creates an annulus, which can be filled by brazing the connection between the two. The difference in I.D.'s between the smaller I.D. of the transition tube 50 and the larger I.D. of the cooling tube 60 creates an expansion point.

Figure 2:
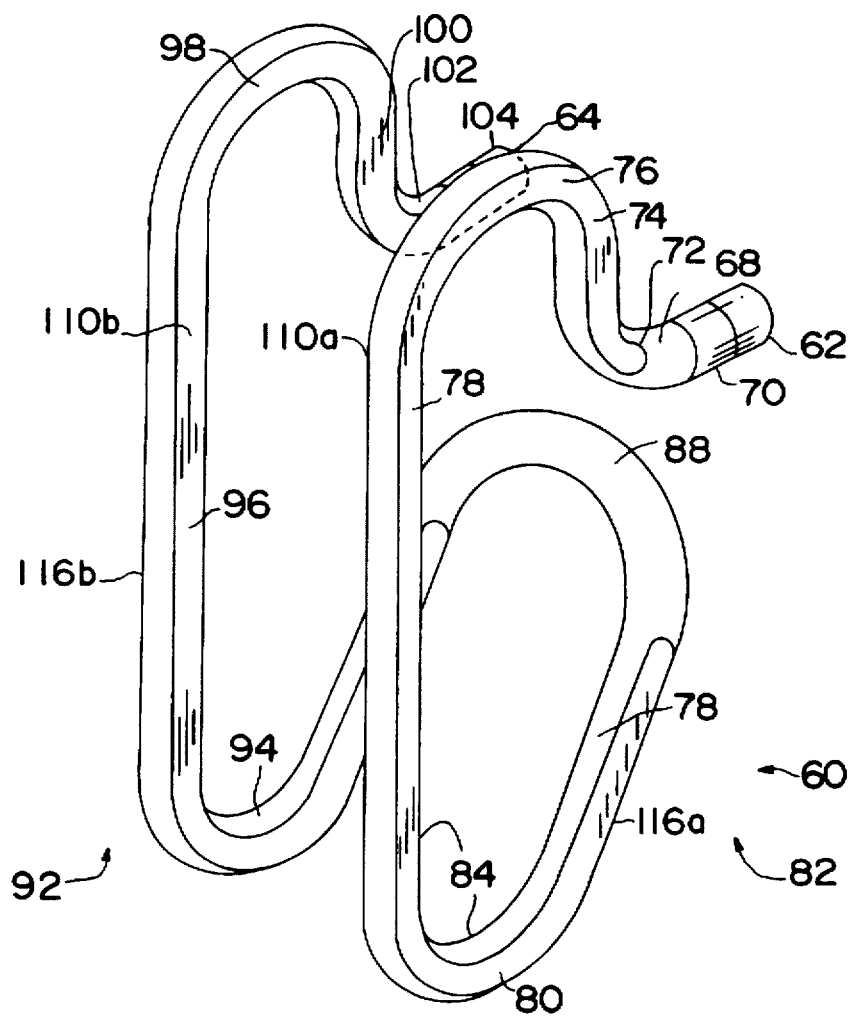
FIG. 2 is an isometric view of a cooling tube according to the present invention.
Figure 3:
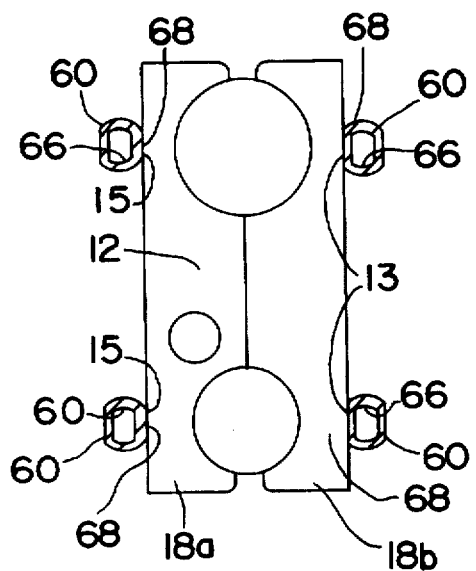
FIG. 3 is a cross-section of a cooling tube, according to the present invention, in engagement with a gas chromatography analyte sample heating block having a split block sandwich.

To create and maximize heat conduction between the coolant and the heating block 12, the cooling tube 60 is configured to physically engage the block 12. More specifically, the cooling tube may be oriented into a series of legs, bends and loops to impart a serpentine structure to maximize physical engagement with the block. Referring now to FIG. 2, in a preferred embodiment, from the receiving end 62 of the cooling tube 60 moving toward the exhaust end 64 there is a receiving leg 70, followed, by a receiving bend 72, followed in turn by a first leg 74, followed in turn by a first loop 76. The cooling tube 60 then has a second leg 78, followed by a second loop 80. The receiving leg 70, the receiving bend 72, the first leg 74, the first loop 76, the second leg 78 and the second loop 80 are substantially co-planar, in a first plane 82, to form a first engagement surface 84, on the outside surface 68 of the cooling tube 60, for physically engaging a first block surface 13 of the heating block 12. Following the second loop 80, the cooling tube has a crossover loop 88 which loops the cooling tube 60 to a second plane 92 which is substantially parallel to the first plane 82. In the second plane 92, the cooling tube 60 has a third loop 94, followed by a third leg 96, followed in turn by a fourth loop 98 and then a fourth leg 100. Following the fourth leg 100, the cooling tube has an exhaust bend 102 and then an exhaust leg 104 leading to the exhaust end 64 of the cooling tube 60. The third loop 94, the third leg 96, the fourth loop 98, the fourth leg 100, the exhaust bend 102, and the exhaust leg 104 are all substantially co-planar in the second plane 92, forming a second engagement surface 106, on the outside surface 68 of the cooling tube 60, for engaging a second block surface 15 of the heating block 12. A linear length of the cooling tube that has been used is about 8 inches, to allow for a serpentine configuration to engage with known heating blocks.

Figure 4A:
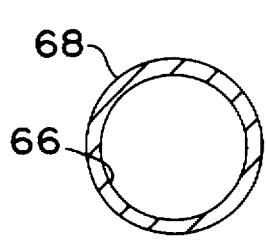
FIGS. 4a and 4b are cross-sectional views of embodiments of a cooling device according to the present invention.
Figure 4B:
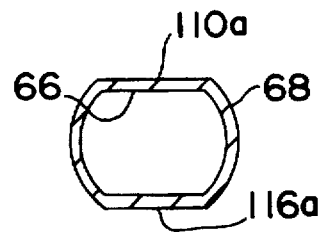

The cooling tube may have a substantially round cross-section, as shown in FIG. 4a. In a preferred embodiment, the cooling tube is partially flattened, as shown in FIG. 4b, to form medial flat surfaces 110a and 110b, and lateral flat surfaces 116a and 116b (referring now again to FIG. 2). The partial flattening of the of the cooling tube 60 is done in a manner such that the flat surfaces at least partially coincide with the engagement surfaces 84 and 106. Preferably, the flat surfaces are configured in such a manner that at least some of the flat surfaces increase the size of each of the engagement surfaces 84 and 106. In one embodiment, flat surfaces 110a and 110b enlarge engagement surfaces 84 and 106.

The cooling tube is mounted so that the first engagement surface 84 engages a first block surface 13 of the heating block 12 and the second engagement surface 106 engages the second block surface 15 of the heating block. With the heating block consisting of a split block pair sandwiched together, the first block surface 13 is typically on a first block section 18a of the block sandwich, and the second block surface 15 is typically on a second block section 18b of the block sandwich. However, it will be appreciated that the cooling device of the present invention may be used with a gas chromatography injector having a monolithic block, in which case the first block surface 13 and the second block surface 15 will simply be on different sides of a monolithic block; or a block consisting of a plurality of block sections. Further, it will be appreciated that the engagement surfaces may be nonparallel and non-planar, and there may be more than two engagement surfaces.

As noted above, preferable materials for the cooling tube 60 are aluminum, copper, silver and gold. In the case of copper, although the heat conductivity level is high, the long-term performance can be diminished due to the propensity of copper to oxidize when exposed to high temperatures, with the oxidized copper having a low thermal conductivity and a low structural integrity so as to be structurally unsound. To prevent oxidation of a copper cooling tube, the cooling tube can coated or plated. A copper cooling tube may be nickel plated, although nickel has been found to have poor thermal conductivity, and thus has an insulating rather than a conductive effect. Alternatively, a composite sandwich of silver/copper/silver can be used to form the cooling tube. Preferably, the cooling tube is configured primarily of silver. Sterling silver can be used; however, due to the copper content of sterling silver, oxidation (in the form of tarnishing) can occur, decreasing effectiveness and increasing maintenance procedures and costs. Fine silver, that is 99.9% pure silver is preferable because it has a favorably high thermal conductivity, 420 watts/meter ° C., and undergoes repeated high temperature cycling without deleterious oxidation, with minimal oxide layer growth and with minimal effect on structural integrity.

Figure 5A:
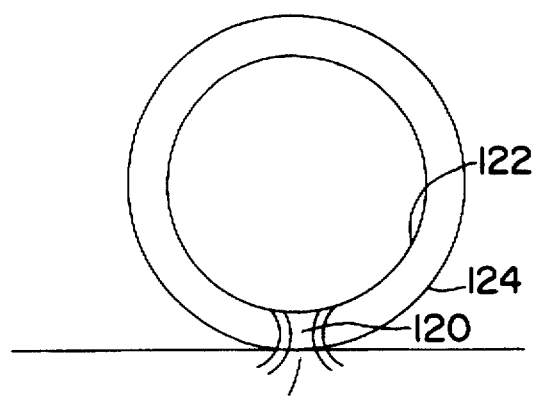
FIGS. 5a–c are schematic comparisons of heat transfer in modular cooling devices for gas cooling chromatography analyte sample heating blocks.
Figure 5B:
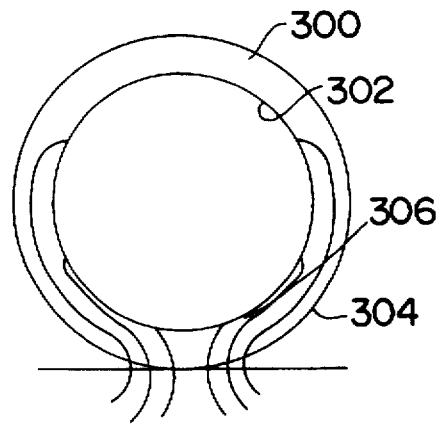
Figure 5C:
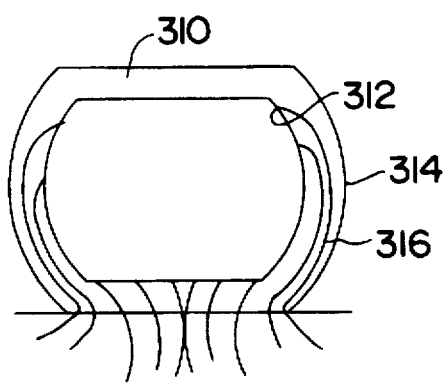

FIG. 5a, shows a schematic cross-sectional representation of the radial and circumferential heat conduction from an inside wall 122 of a known cooling fluid tube configured of stainless steel to an outside wall 124 thereof. The effective heat exchange region of the known cooling fluid tube is substantially limited to a narrow wedge 120 of heat exchange extending from the inside wall 122 to the outside wall 124. In the present invention, the effective heat exchange region of the cooling tube is widened, as shown in FIG. 5b in which a cross-sectional schematic representation of an embodiment of the present invention showing a cooling tube 300 having and inside surface 302 and an outside surface 304 in which a heat transfer wedge 306 is shown. FIG. 5c shows a cross-sectional schematic representation of another embodiment of a cooling device of the present invention with a cooling tube 310 having and inside surface 312 and an outside surface 314 in which a heat transfer wedge 316 is shown.

An exhaust 69 (FIGS. 1 and 2a), preferably made of stainless steel, is connected to the exhaust end 64 of the cooling tube 60. The exhaust 69 that has been used has been of 0.094 I.D. and 0.126 O.D., the same dimensions as have been used for Ad; the transition tube of the $LN_2$ configuration, for exhausting both $LN_2$ and $LCO_2$ configurations. The exhaust 69 may be connected to the exhaust end 64 of the cooling tube 60 by brazing.

Figure 6:
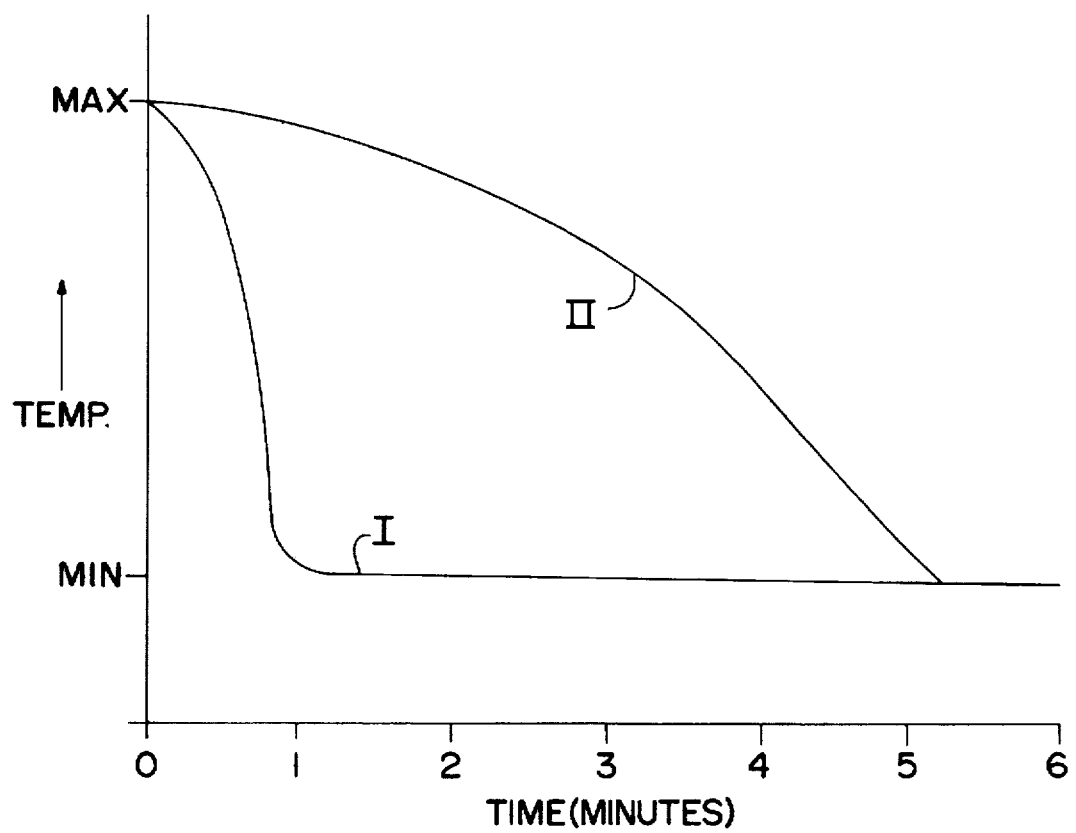
FIG. 6 is a graphical comparison of the cooling effect of a known modular cooling device and a cooling device according to the present invention.

Testing results for the cooling device of the present invention have shown an improvement of cooling rate over known cooling devices in which the heating block is externally cooled by a coolant tube. The improvement of cool down rate in the cooling device of the present invention is shown graphically in FIG. 6 which plots the decrease in temperature of the block over time. Typically, the test results have shown a cooling rate in a cooling device according to the present invention (plot line I) exceeding five times the cooling rate of known external coolant tube cooling devices (plot line II), approaching and exceeding the cooling efficiency of known internally cooled heating block cooling devices.

Figure 7:
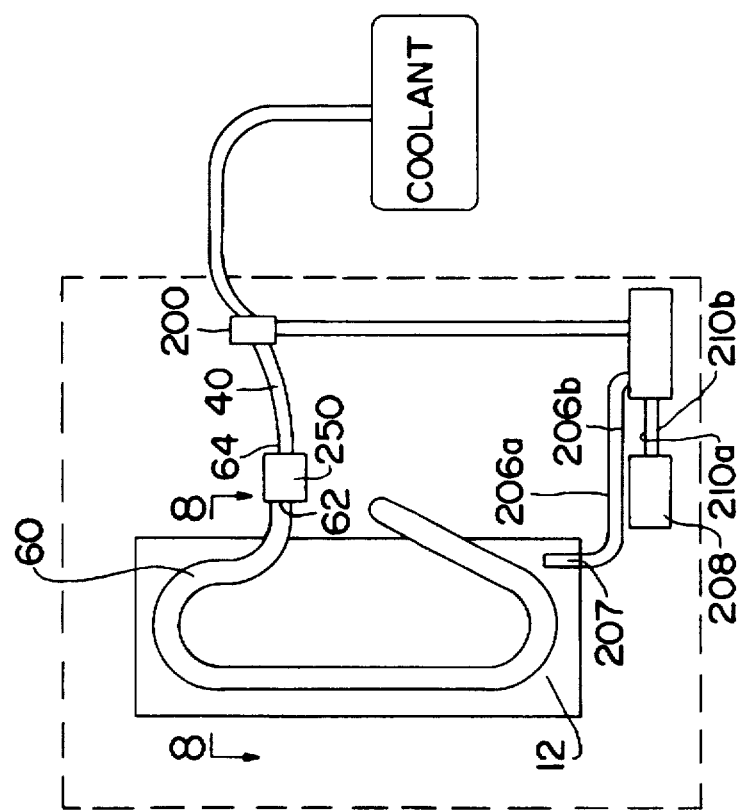
FIG. 7 is a schematic representation of a further another embodiment of a cooling device according to the present invention.

In another embodiment of the present invention (referring now to FIG. 7), the transition tube is eliminated, and receiving end 62 of the cooling tube 60 is connected in fluid communication with the second end 44 of the supply tube 40 through connection 250. In this embodiment, a typical connector can be used to connect the cooling tube to the supply tube. With a supply tube made of PEEK connected to a cooling tube of fine silver, a union with one end that fits the supply tube and one end that fits the cooling tube may be used. The cooling tube may necked down and crimped to fit the supply tube with a crimped fit. It is desirable to have such a connection placed as close to the injector block to reduced the pressure drop associated with the larger internal diameter of the cooling tube.

Figure 8:
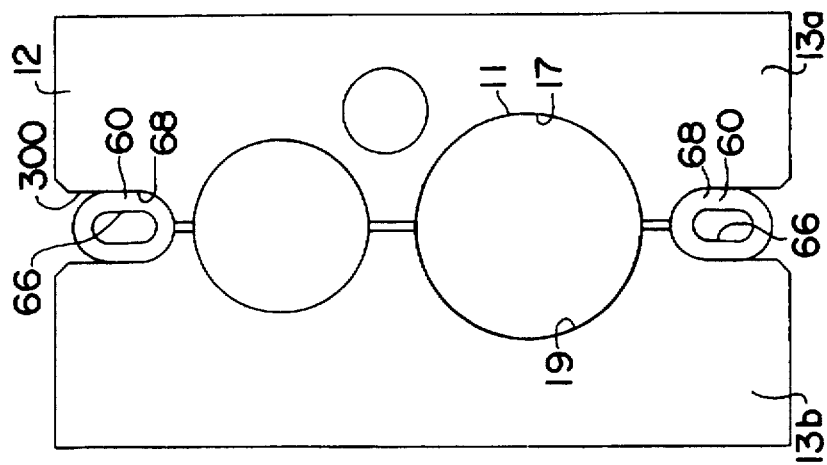
FIG. 8 is a cross-section as in FIG. 3 according to another embodiment of the present invention.
Figure 9:
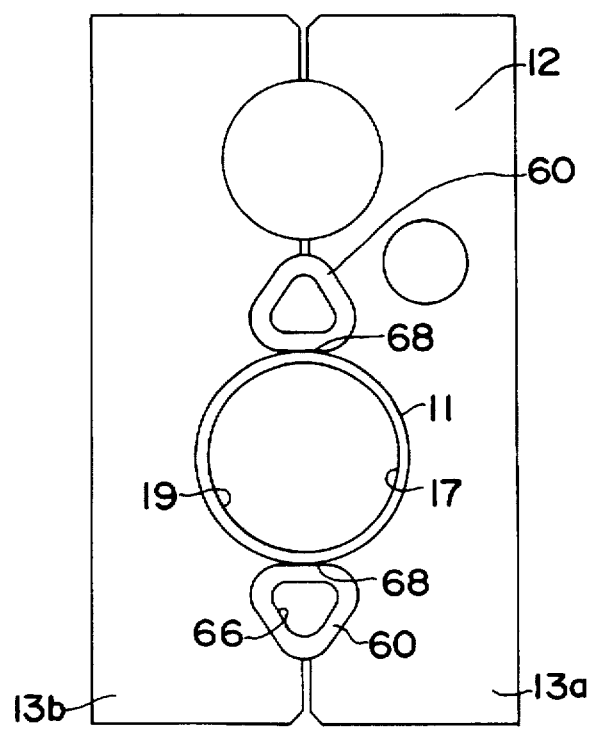
FIG. 9 is a cross-section as in FIG. 3 according to another embodiment of the present invention.

Referring now to FIG. 8, in another embodiment of the present invention, the cooling tube 60 is received in a channel 300 of the block 12. The cooling tube 60 may further be sandwiched in between segments 13a and 13b of the heating block sandwich 12 as shown in FIG. 8. Referring to FIG. 9, in another embodiment of the present invention, the cooling tube 60 is engageable in physical contact with the injector wall 11.

While the present invention has been particularly described with respect to the illustrated embodiment, it will be appreciated that various alterations, modifications and adaptations may be made based on the present disclosure, and are intended to be within the scope of the present invention. While the invention has been described in connection with what is presently considered to be the most practical and preferred embodiment(s), it is to be understood that the present invention is not limited to the disclosed embodiment(s) but, on the contrary, is intended to cover various modifications and equivalent arrangements included within the scope of the appended claims.

What is claimed is:

1. A cooling apparatus for cooling a gas chromatography analyte sample injector, comprising:
    a coolant delivery pathway for carrying coolant from a coolant supply to the gas chromatography injector, said delivery pathway having
        a supply tube, said supply tube being flexible to allow elastic deformation, and
        a cooling tube connected in fluid communication with said supply tube, said cooling tube having a thermal conductivity of at least about 200 watts/meter ° C., said cooling tube configured such that at least a portion of said cooling tube is engageable in physical contact with a portion of the injector to permit heat exchange between cooling fluid flowing within the cooling tube and the injector; and
    a coolant exhaust, in fluid connection with said cooling tube, for exhausting coolant away from the injector.

2. The cooling apparatus of claim 1, wherein said supply tube is capable of maintaining structural integrity over a temperature range of about −100° C. to about 200° C.

3. The cooling apparatus of claim 1, wherein said supply tube is capable of maintaining structural integrity over a temperature range of about −100° C. to about 250° C.

4. The cooling apparatus of claim 1, wherein said supply tube is sufficiently flexible to allow elastic deformation.

5. The cooling apparatus of claim 1, wherein the supply tube consists essentially of a plastic material and the cooling tube consists essentially of silver.

6. The cooling device according to claim 1 wherein the cooling tube has a flattened surface engageable in physical contact with the injector.

7. The cooling device according to claim 1 wherein the cooling tube is composed of a material consisting essentially of silver.

8. The cooling device according to claim 1 wherein the cooling tube consists essentially of fine silver.

9. A cooling apparatus for cooling a gas chromatography injector, comprising:
    a coolant delivery pathway for carrying coolant from a coolant supply to the gas chromatography injector, said delivery pathway having
        a supply tube, said supply tube useable capable of maintaining structural integrity over a temperature range of about −100° C. to about 250° C., having a thermal conductivity no greater about 100 watts/meter ° C. and having a flexibility to allow elastic deformation, said supply tube for carrying coolant from a coolant supply to a transition tube, and
        a transition tube connected in fluid communication with said supply tube, said transition tube being useable capable of maintaining structural integrity in a temperature range from about −100° C. to 450° C., having a temperature conductivity no greater about 100 watts/meter ° C., said transition tube for carrying coolant from said supply tube to a region adjacent to the heating block, and
        a cooling tube connected in fluid communication with said transition tube, said cooling tube being useable in a temperature range from about −100° C. to about 450° C., having a thermal conductivity of at least about 200 watts/meter ° C., and having sufficient ductility to allow manipulation into a predetermined configuration and rigidity to maintain a predetermined configuration, said cooling tube configured such that at least a portion of said cooling tube is engageable in physical contact with the heating block, said cooling tube for carrying coolant from said transition tube to the heating block; and
    a coolant exhaust, in fluid connection with said cooling tube, for exhausting coolant away from the heating block.

10. The cooling apparatus of claim 9, wherein said supply tube is sufficiently flexible to allow elastic deformation.

11. The cooling apparatus of claim 9, wherein the supply tube consists essentially of plastic, and the cooling tube consist essentially of silver.

12. The cooling device according to claim 9, wherein the cooling tube has a flattened surface engageable in physical contact with the heating block.

13. The cooling device according to claim 9, wherein the cooling tube is composed of a material consisting essentially of silver.

14. The cooling device according to claim 9, wherein the cooling tube consists essentially of fine silver.

15. A cooling apparatus for cooling a gas chromatography injector, comprising:
    a coolant delivery pathway for carrying coolant from a coolant supply to the gas chromatography injector, said delivery pathway having a supply tube and a cooling tube connected in fluid communication with said supply tube, said cooling tube at least partially engageable in physical contact with the injector;
    wherein the supply tube is more flexible than the cooling tube and the cooling tube has a greater temperature conductivity than the supply tube.

16. The cooling apparatus of claim 15, wherein said supply tube is sufficiently flexible to allow elastic deformation.

17. The cooling apparatus of claim 15, wherein the supply tube consists essentially of plastic, and the cooling tube consist essentially of silver.

18. The cooling device according to claim 15, wherein the cooling tube has a flattened surface engageable in physical contact with the heating block.

19. The cooling device according to claim 15, wherein the cooling tube is composed of a material consisting essentially of silver.

20. The cooling device according to claim 15, wherein the cooling tube is consists essentially of fine silver.

21. A cooling apparatus for cooling a gas chromatography passage; heatable zone, comprising:

a coolant delivery pathway for carrying coolant from a coolant supply to the gas chromatography passage; heatable zone, said delivery pathway having a supply tube, a transition tube connected in fluid communication with said supply tube, and a cooling tube in fluid communication with the transition tube, said cooling tube having a portion engageable in physical contact with the heating block;

wherein the supply tube is more flexible than the transition tube and the cooling tube and the cooling tube has a greater heat conductivity than the transition tube and the supply tube.

22. The cooling apparatus of claim 21, wherein said supply tube is sufficiently flexible to allow elastic deformation.

23. The cooling apparatus of claim 21, wherein the supply tube consists essentially of plastic, and the cooling tube consist essentially of silver.

24. The cooling device according to claim 21, wherein the cooling tube has a flattened surface engageable in physical contact with the heating block.

25. The cooling device according to claim 21, wherein the cooling tube is composed of a material consisting essentially of silver.

26. The cooling device according to claim 21, wherein the cooling tube consists essentially of fine silver.

* * * * *